United States Patent
Piantoni et al.

(10) Patent No.: US 10,342,709 B2
(45) Date of Patent: Jul. 9, 2019

(54) MACHINE FOR MAKING ABSORBENT SANITARY ARTICLES

(75) Inventors: Matteo Piantoni, Albino (IT); Alberto Perego, Milan (IT)

(73) Assignee: GDM S.p.A., Bologna (IT)

( * ) Notice: Subject to any disclaimer, the term of this patent is extended or adjusted under 35 U.S.C. 154(b) by 742 days.

(21) Appl. No.: 14/238,574

(22) PCT Filed: Sep. 6, 2012

(86) PCT No.: PCT/IB2012/054617
§ 371 (c)(1),
(2), (4) Date: Feb. 12, 2014

(87) PCT Pub. No.: WO2013/035067
PCT Pub. Date: Mar. 14, 2013

(65) Prior Publication Data
US 2014/0249010 A1    Sep. 4, 2014

(30) Foreign Application Priority Data
Sep. 8, 2011 (IT) .............................. BO2011A0512

(51) Int. Cl.
*A61F 13/15* (2006.01)
*B65H 35/04* (2006.01)
*B65H 39/14* (2006.01)

(52) U.S. Cl.
CPC .. *A61F 13/15577* (2013.01); *A61F 13/15756* (2013.01); *A61F 13/15764* (2013.01);
(Continued)

(58) Field of Classification Search
CPC .......... A61F 13/15756; A61F 13/15764; A61F 13/15577; B65H 35/04; B65H 39/14
(Continued)

(56) References Cited

U.S. PATENT DOCUMENTS 6,811,019 B2    11/2004   Christian et al.
8,790,232 B2     7/2014   Pastrello et al.
(Continued)

FOREIGN PATENT DOCUMENTS

CN       1860075    11/2006
CN     102076584     5/2011
(Continued)

OTHER PUBLICATIONS

Office Action issued by the Chinese Patent Office dated Jun. 10, 2015 for related Chinese Patent Application No. 201280043711.6.
(Continued)

*Primary Examiner* — Michelle Lopez
*Assistant Examiner* — Chinyere J Rushing-Tucker
(74) *Attorney, Agent, or Firm* — Shuttleworth & Ingersoll, PLC; Timothy J. Klima

(57) ABSTRACT

A machine for making absorbent sanitary articles includes a feed conveyor on which a continuous web of material for making the articles is advanced along a feed line in a first direction. A forming and application unit forms and applies by which at least one pair of accessory elements for each article and includes a device for feeding a continuous succession of accessory elements and a conveying unit. The conveying unit includes a conveyor roller for the continuous succession of accessory elements, and a separating device defined by a first and a second spacer roller which are substantially tangent to the conveyor roller at a first and a second pickup station, respectively. The first and the second spacer roller have retaining and alternate movement devices including respective pickup pads which are slidable along a second direction and which are driven by a respective linear electric motor.

20 Claims, 6 Drawing Sheets

(52) U.S. Cl.
CPC ............. *B65H 35/04* (2013.01); *B65H 39/14* (2013.01); *B65H 2402/10* (2013.01); *B65H 2406/34525* (2013.01); *B65H 2555/132* (2013.01); *B65H 2601/324* (2013.01); *B65H 2801/57* (2013.01)

(58) Field of Classification Search
USPC ........................................................ 493/343
See application file for complete search history.

(56) References Cited

U.S. PATENT DOCUMENTS

| | | | |
|---|---|---|---|
| 2002/0023723 A1* | 2/2002 | Blumenthal | A61F 13/15764 156/530 |
| 2004/0099114 A1 | 5/2004 | Bridges et al. | |
| 2004/0245069 A1 | 12/2004 | Hook et al. | |
| 2004/0262127 A1 | 12/2004 | Harnish et al. | |
| 2007/0256777 A1* | 11/2007 | Andrews | A61F 13/15756 156/163 |
| 2008/0196564 A1 | 8/2008 | McCabe | |
| 2010/0192739 A1* | 8/2010 | Piantoni | A61F 13/15756 83/26 |
| 2010/0258240 A1* | 10/2010 | McCabe | A61F 13/15756 156/226 |
| 2010/0270126 A1 | 10/2010 | Piantoni et al. | |
| 2011/0088233 A1 | 4/2011 | McCabe et al. | |
| 2012/0190523 A1* | 7/2012 | Pastrello | A61F 13/15756 493/343 |
| 2013/0239765 A1* | 9/2013 | McCabe | A61F 13/15723 83/100 |
| 2013/0270065 A1* | 10/2013 | Papsdorf | A61F 13/15764 198/377.01 |
| 2015/0297416 A1* | 10/2015 | Piantoni | A61F 13/15756 156/517 |
| 2016/0106597 A1* | 4/2016 | Long | A61F 13/15764 198/617 |

FOREIGN PATENT DOCUMENTS

| | | |
|---|---|---|
| EP | 0450650 | 10/1991 |
| WO | 2008/155618 | 12/2008 |
| WO | 2010/001361 | 1/2010 |

OTHER PUBLICATIONS

International Search Report dated Nov. 19, 2012 from counterpart PCT App. No. PCT/IB2012/054617.
Korean Office Action dated Jul. 6, 2018 from counterpart KR App No. 10-2014-7009335.
Japanese Office Action dated Apr. 26, 2016 from counterpart JP App No. 2014-529119.

* cited by examiner

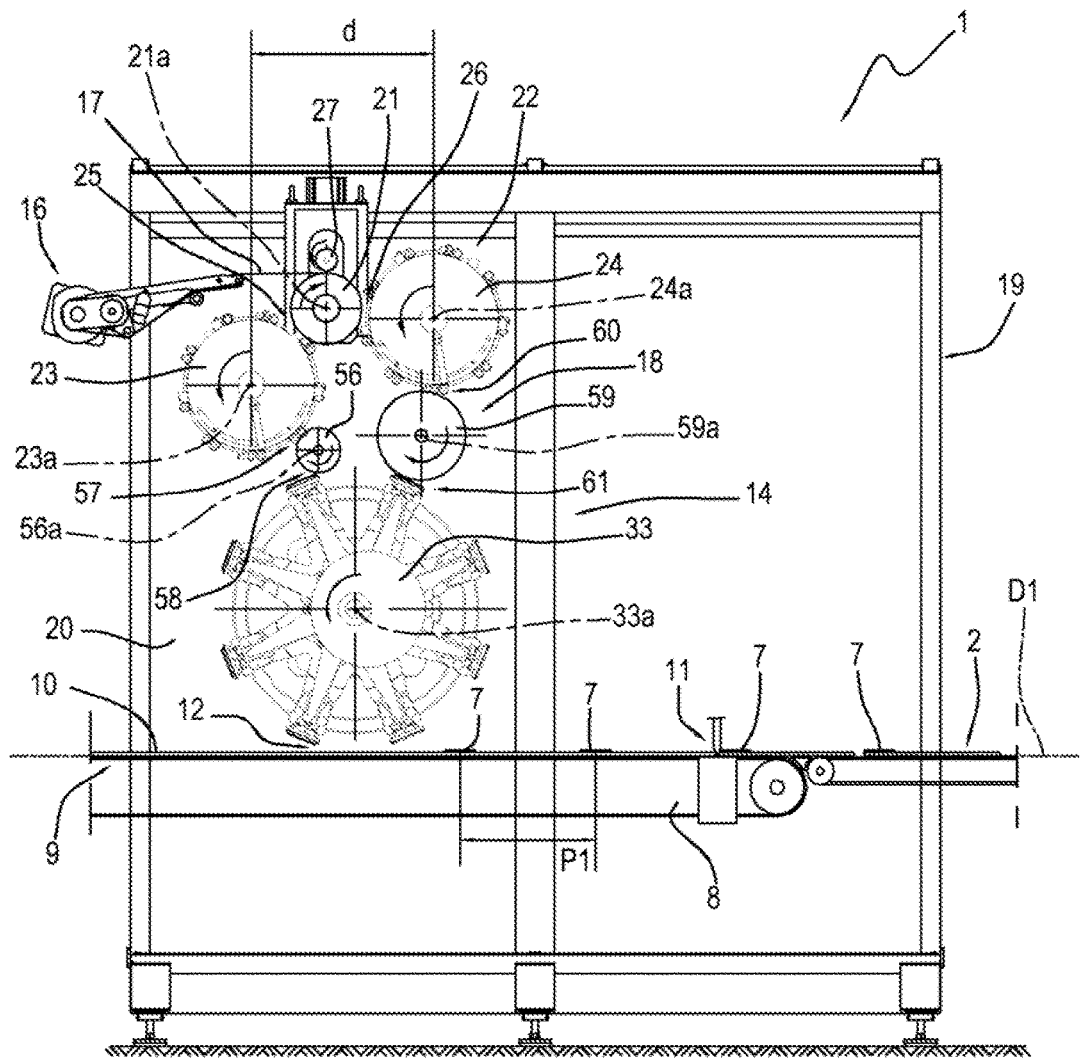

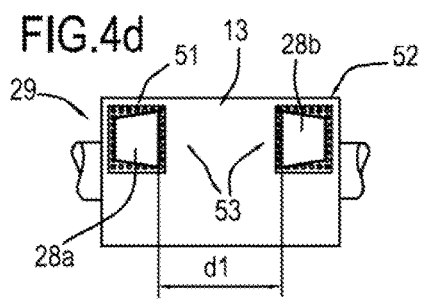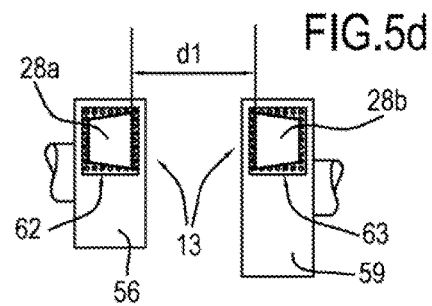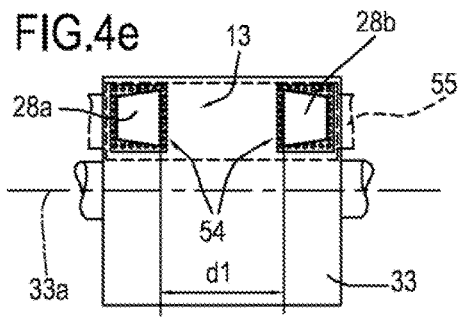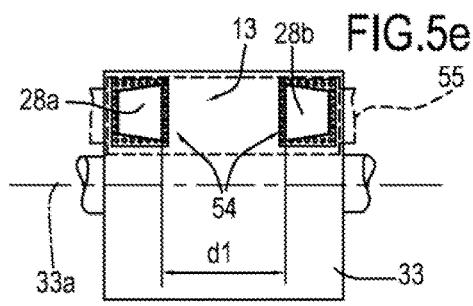

MACHINE FOR MAKING ABSORBENT SANITARY ARTICLES

This application is the National Phase of International Application PCT/IB2012/054617 filed Sep. 6, 2012 which designated the U.S. and that International Application was published under PCT Article 21(2) in English.

This application claims priority to Italian Patent Application No. BO2011A000512 filed Sep. 8, 2011, the entirety of which is incorporated by reference herein.

TECHNICAL FIELD

This invention relates to a machine for making absorbent sanitary article.

More specifically, the invention relates to a machine for making absorbent sanitary articles such as disposable nappies for children or adults.

BACKGROUND ART

As is known, these articles are obtained by laying a sheet of impermeable material over a sheet of permeable material (of non-woven fabric), with a padding consisting of an absorbent pad interposed between the two sheets. More specifically, both in the case of nappies of children and in the case of nappies for adults, it is usual to add accessory components such as lateral flaps for closing the nappy round the wearer's waist.

Generally speaking, in a prior art machine, the lateral closure flaps are applied along certain stretches of a continuous web of a material for making nappies, these stretches corresponding to the single nappies, when subsequently divided.

Patent application WO2010001361A1, in the name of the same Applicant as this invention, describes a machine for making absorbent articles of the above mentioned kind.

The machine comprises a unit for forming and applying pairs of ateral flaps to the continuous web.

This unit is equipped, at its upper end, with a device for cutting a continuous web of elatomeric material into suitably shaped single pieces constituting the lateral flaps for closing the nappies.

The cutting device is substantially tangent to a first and a second roller. The first and second rollers both have suction pads which pick up the single flaps cut by the cutting device in such a way as to form respective successions of single, equioriented flaps. Further, the suction pads are slidable between two end positions along, a direction parallel to the axis of the respective roller, in such a way as to space the single flaps by a length which is less than the transversal dimension of the continuous web of nappies.

The single flaps, conveyed one after the other from the first roller to the second, are transferred to the same receiving roller which is tangent to both of the rollers and located downstream of them.

The first and second rollers feed the respective single flaps to pairs of suctions seats on the receiving roller which thus form the pair of lateral flaps intended for each single nappy.

The suction seats on the receiving roller are also slidable along a direction parallel to the axis of the roller itself, in order to further space the single flaps until reaching the predetermined spacing along the waistline of the nappies.

Once the pairs of flaps formed have been further spaced by the receiving roller, they are transferred from the receiving roller to an accelerator roller which conveys each pair of lateral flaps in step and applies them to the continuous web.

Both the slidable pads of the first and second rollers and the slidable seats of the receiving roller are mechanically driven by cam means.

The size of a nappy defines the spacing of the lateral flaps and further defines the size of each single lateral flap.

In the unit of the type described, when the spacing of the lateral flaps varies, the length by which the slidable pads of the separating device and the suction seats of the receiving roller must be moved also varies.

The cam means which drive the slidable pads and the suction seats are limited in movement so that the spacing they can create according to the size of the nappy being made can only be varied to limited extents. More specifically, the cam means which create the lateral flap spacing for children's nappies cannot create the lateral flap spacing required for nappies to be used by adults.

As a result, changing over to making nappies of a different size necessitates substituting the first and second rollers of the separating device and the receiving roller for similar rollers equipped with cam means suitable for creating the spacing required by the size of the nappy to be made.

Moreover, the size of a single lateral flap, in particular the longitudinal length of the single flap, defines the size of the slidable pads and of the suction seats.

Since the slidable pads and the suction seats cannot be substituted when the longitudinal length of the lateral flap varies, changeover involves entirely substituting the rollers of the separating device and the receiving roller for similar rollers equipped with slidable pads and suction seats of suitable size. More specifically, increases in the longitudinal dimension of the lateral flaps mean increases in their radial dimension, which in turn means increases in the radial dimensions of the respective rollers.

As a result, when the size of the lateral flaps must be varied, it is necessary not only to substitute the rollers but also to vary the distance of the roller axes from each other so as to reposition them suitably according to their radial dimensions.

Repositioning the rollers is a structurally complex operation which involves extended machine downtimes, since the rollers of the separating device and the receiving roller are mechanically complex parts of considerable size.

DISCLOSURE OF THE INVENTION

This invention has for an aim to provide a machine for making absorbent sanitary articles which can be easily adapted to make nappies of different sizes, such as, for example, nappies for children and for adults, and more specifically, a machine which limits the need to substitute the rollers of the lateral flap forming and application unit upon changeover to a different nappy size.

The above mentioned technical purpose and aims are achieved by a machine having the technical features described in the independent claim 1.

BRIEF DESCRIPTION OF THE DRAWINGS

Further features and advantages of this invention are more apparent in the description below, with reference to a preferred, non-limiting embodiment of a machine as illustrated in the accompanying drawings, in which:

FIG. 2 is a schematic front view illustrating a second embodiment of the machine of FIG. 1;

FIGS. 4a, 4b, 4c, 4d and 4e schematically illustrate steps in the operation of the machine according to the embodiment of FIG. 1;

FIGS. 5a, 5b, 5c, 5d and 5e schematically illustrate steps in the operation of the machine according to the embodiment of FIG. 2;

DETAILED DESCRIPTION OF THE PREFERRED EMBODIMENTS OF THE INVENTION

Figure 1:
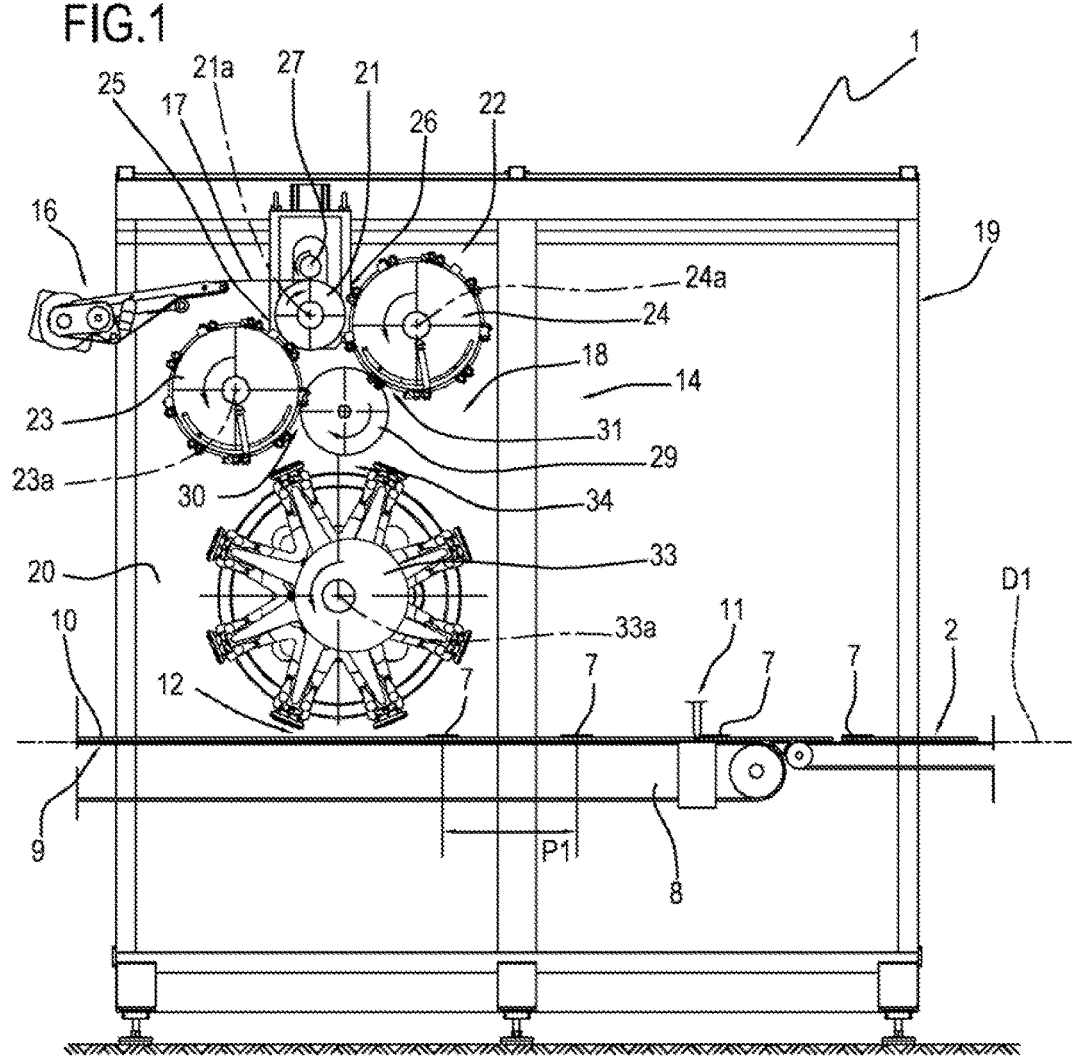
FIG. 1 is a schematic front view illustrating a machine for making absorbent sanitary articles according to this invention.

With reference to FIGS. 1 and 2, the numeral 1 denotes in its entirety a machine for making absorbent sanitary articles 2.

Figure 1A:
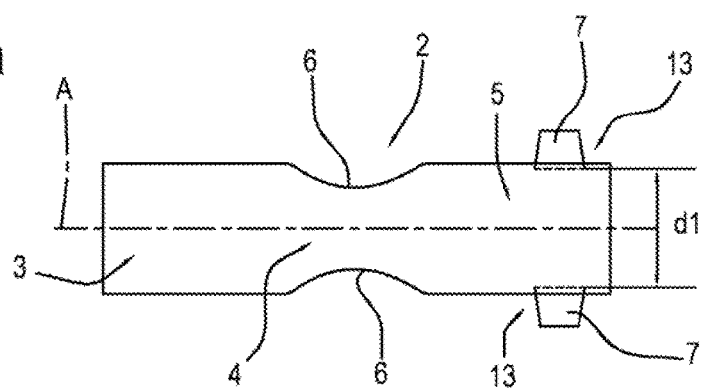
FIG. 1a is a schematic plan view of an absorbent sanitary article made by the machine according to the invention.

The absorbent sanitary articles 2 are substantially rectangular hope and extend along a longitudinal axis A, as shown in FIG. 1a.

The absorbent sanitary articles 2 comprise, in a line along the axis A front portion 3, a central portion 4 and a rear portion 5.

At the central portion 4, the article 2 has a recess 6, or thigh opening, defined by two arcuate sections which are symmetrical about the axis A.

The absorbent articles 2 comprise an internal absorbent padding, normally made from cellulose fibres, placed inside a soft container defined on one side by a permeable sheet of non-woven fabric and, on the other side, by an impermeable sheet of polyethylene.

The absorbent article 2 also has two accessory elements 7, or lateral flaps, extending transversely to the axis A. More precisely, the lateral flaps 7 extend from the rear portion 5 of the absorbent article 2 and are, in use, designed to be placed over respective fastening zones of the front portion 3 in order to close the absorbent article 2 round the wearer's hips.

The lateral flaps 7 generally consist of pieces 28 of sheet material, preferably elastic material, and have a surface which is partly covered with an adhesive substance, or provided with other quick fastening means.

It should be noted that the accessory elements 7 which, as mentioned above, define the lateral flaps and are denoted by the same reference numeral 7, therefore also consist of the pieces 28 of sheet material. In other words, in this specific case, the accessory elements and the lateral flaps coincide and both consist of pieces 28 of sheet material.

The machine 1 comprises a feed conveyor 8 on which a continuous web 10 of material for making the absorbent articles 2 is advanced along a feed line 9 in a first direction D1.

The feed line 9 extends horizontally as far as a cutting element 11 by which the continuous web 10 is divided into single lengths that will make up single absorbent articles 2.

Along the feed conveyor 8, upstream of the cutting element 11, there is a feed station 12 for feeding pairs 13 of lateral flaps 7 which are applied at a predetermined spacing P1 along the continuous web 10.

The machine 1 comprises a forming and application unit 14 by which the pairs 13 of accessory elements 7 are formed and applied to predetermined zones of the continuous web 10 and spaced from each other by a spacing P1 along the feed line 9. The spacing P1 coincides with the spacing of the lengths of the web 10 which will constitute the single absorbent articles 2.

With reference in particular to FIG. 1, the forming and application unit 14 comprises a device 16 for feeding a continuous succession 17 of accessory elements 7 and a conveying unit 18 comprising a plurality of conveyors 21, 22, 29 rotating about respective axes parallel to a second direction D2 transversal to the feed direction D1 of the continuous web 10.

A base 19, delimited at the front by a vertical wall 20, constitutes the support for the rotary conveyors 21, 22, 29 mounted with the respective axes transversal to the vertical wall 20 itself.

The conveying unit 18 comprises a conveyor roller 21 for the continuous succession 17 of accessory elements 7.

A cutting roller 27, which rotates in an anticlockwise direction, acts in conjunction with the conveyor roller 21, which rotates in a clockwise direction about its axis 21a in order to make the continuous succession 17 of pieces 28.

The cutting roller 27 is equipped with a pair of blades which are skew to each other and inclined transversely to the axis of rotation of the roller 27 itself. The blades positioned in this way makes cuts which are oblique relative to the longitudinal direction of the continuous succession 17, thus forming substantially trapezoidal pieces 28.

For greater clarity, in FIGS. 4a to 4e and 5a to 5e, the reference label 28a indicates the pieces whose long base is directed towards the right, and the reference label 28b the pieces whose long base is directed towards the left, relative to the longitudinal axis B of the succession 28.

The conveying unit 18 comprises a separating device 22 defined by a first and a second spacer roller 23 and 24 which are substantially tangent to the conveyor roller 21 at a first and a second pickup station 25 and 26, respectively.

In the preferred embodiment of the machine 1, illustrated in FIG. 1, the conveying unit 18 comprises a forming roller 29 for the pairs 13 of accessory elements 7 and substantially tangent to the first and second spacer rollers 23 and 24 at a first and a second releasing station 30 and 31, respectively. The forming roller 29 can receive respective accessory elements 7 from the first and second spacer rollers 23 and 24 and make up a succession of pairs 13 of accessory elements 7 aligned with each other along the second direction D2.

The numeral 33 denotes an accelerator roller which is substantially tangent to the forming roller 29 for the pairs 13 of accessory elements 7 at a first transfer station 34. The accelerator roller 33, which rotates anticlockwise about its axis 33a, is also tangent to the feed conveyor 8 at the feed station 12.

Figure 3:
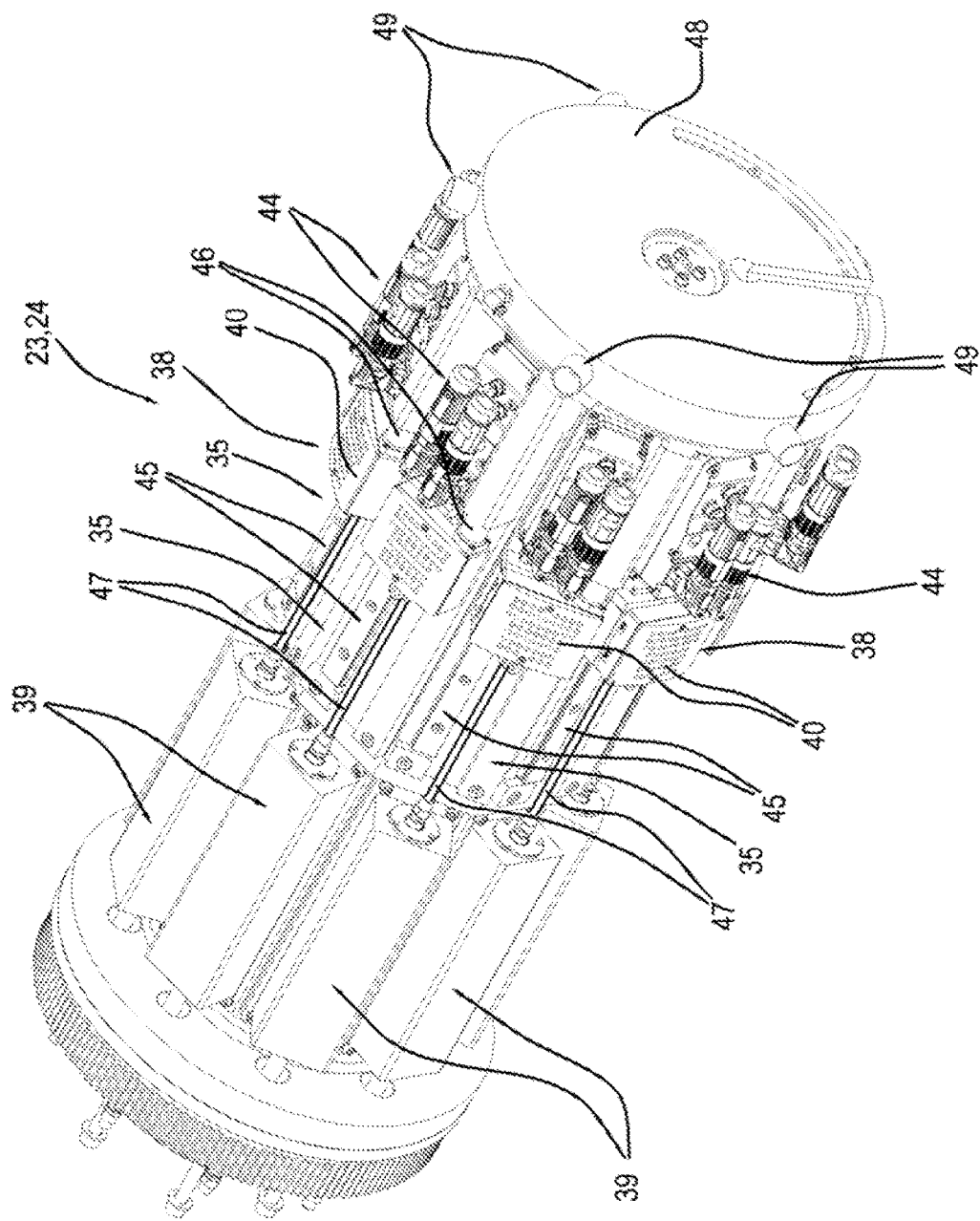
FIG. 3 is a perspective view of a detail of the machine illustrated in FIGS. 1 and 2.
Figure 4A:
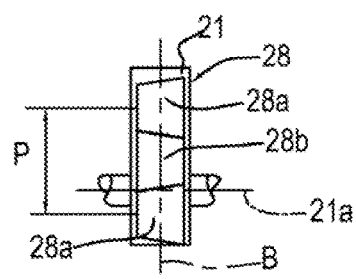
Figure 5A:
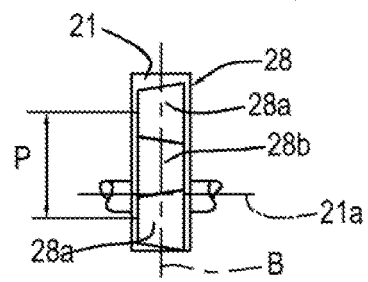
Figure 4B:
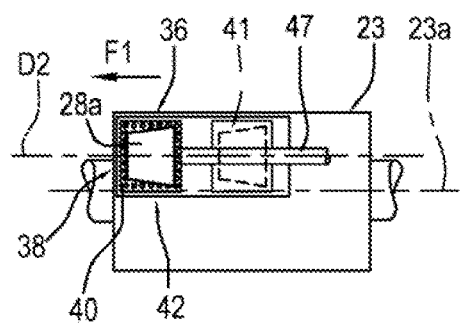
Figure 5B:
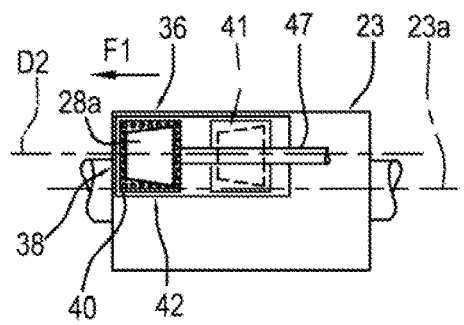
Figure 4C:
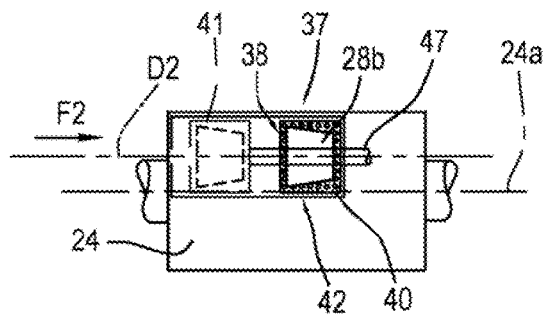
Figure 5C:
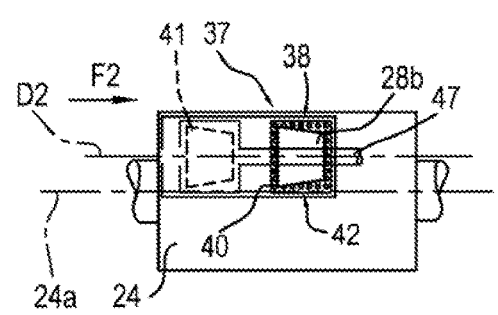
Figure 6:
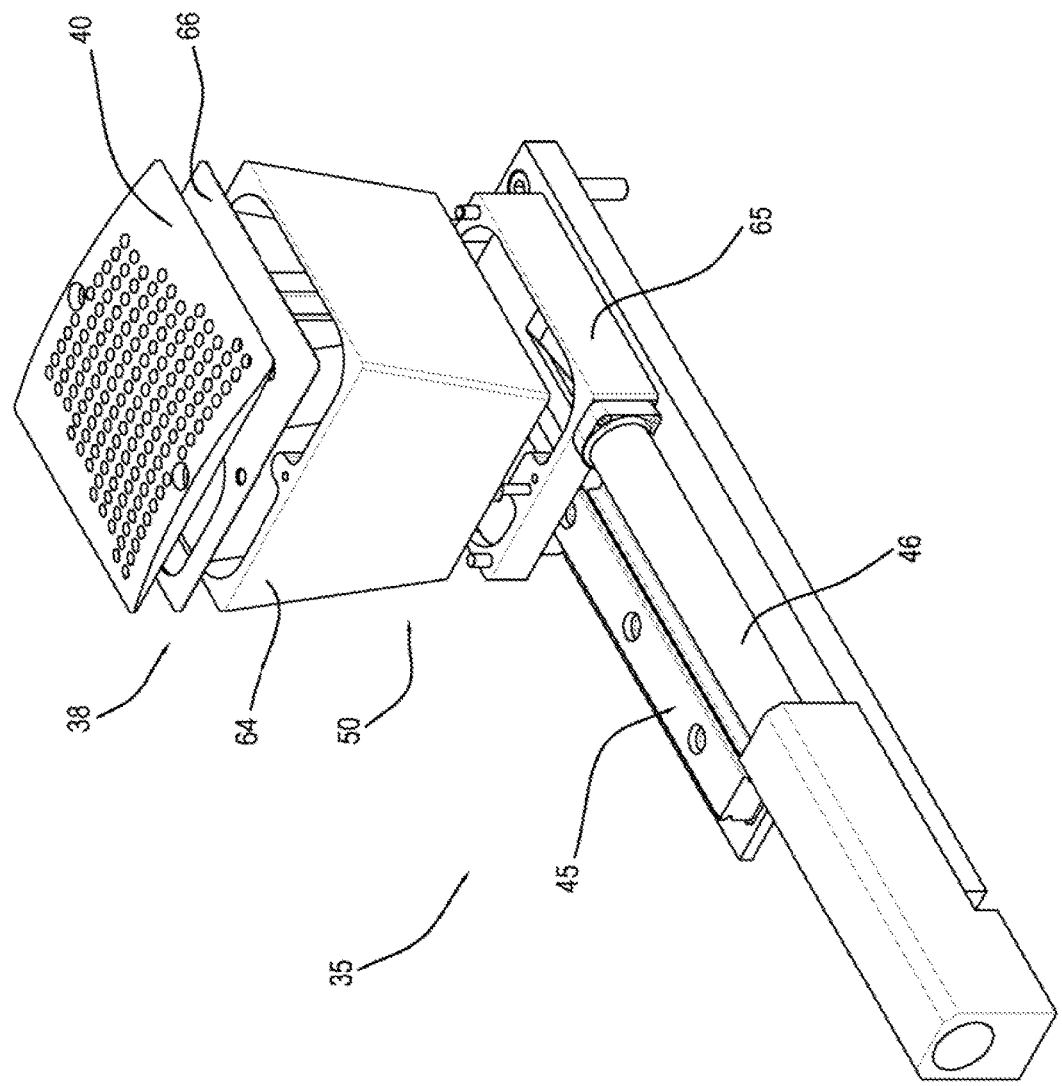
FIG. 6 is a perspective view of a detail from FIG. 3.

The first and second spacer rollers 23 and 24, which both rotate anticlockwise about their respective axes 23a and 24a, are substantially the same. As illustrated in FIGS. 3 and 6, the first and second spacer rollers 23 and 24 have retaining and alternate movement means 35 by which single accessory elements are alternately held and moved along a direction parallel to the second direction D2 in order to form respective successions 36 and 37 of accessory elements.

The retaining and alternate movement means 35 comprise respective pickup pads 38 which are slidable along the second direction D2. More specifically, each pad 38 is driven by a respective linear electric motor 39.

Each pickup pad 38 is movable from a first, receiving position 41 to a second, releasing position 42.

The second releasing position 42 of each pickup pad 38 defines a mutual spacing d1 between the accessory elements 7, equal to the spacing of the accessory elements 7 of the article 2.

In other words, the second releasing position 42 is strictly dependent on the size of the article 2 and, consequently, on the transversal dimension of the continuous web 10.

Each linear motor 39 is associated with a control unit 44 mounted on the cylindrical surface of the respective roller 23 and 24. Wiring not illustrated connects each control unit 44 to the respective linear motor 39.

Each pickup pad 38 runs in a respective guide 45 and is linked to a conduit 46 connected to source of suction, not illustrated, and to an actuating rod 47 of the respective linear motor 39.

The rod 47 is of a size such as to define the stroke of the pickup pad 38 so the stroke is equal in length to the distance between the first receiving position 41 and the second releasing position 42. More specifically, the first receiving position 41 and the second releasing position 42 are located each at a respective end of the stroke of the rod 47.

More specifically, the spacer rollers 23 and 24 differ in the length of the rod 47, the rod 47 of the spacer roller 23 being equal in length to the longest stroke achievable by the unit 1.

The source of suction, not illustrated, is in fluid communication with a cylindrical cam 48 through a plurality of inlets 49. The inlets 49 are located along the outer cylindrical surface of the cam 48 and extend radially therefrom.

The conduits 46 are in fluid communication with the cylindrical cam 48 and, consequently, each pad 38 is in fluid communication with the suction source not illustrated. More specifically, the surface 40 of the pickup pad 38 for each accessory element 7 is a suction surface.

Each of the retaining and alternate movement means 35 comprises a mounting unit 50 for the respective pickup pad 38.

The mounting unit 50 is interchangeable with variations in the size of the pickup pad 38 according to the size of the accessory element 7. More specifically, it is interchangeable according to the longitudinal length of the accessory element 7.

The mounting unit 50 of the pickup pad 38 is defined by a central body 64 connected to a respective fixed insert 65. The fixed insert 65 is connected to the respective conduit 46 and runs in the respective guide 45.

The central body 64 is interchangeable with variations in the size of the pickup pad 38 according to the size of the accessory element 7. The central body 64 comprises an interface plate 66 and the receiving surface 40 of the respective accessory element 7 is connected to the interface plate 66.

Alternatively, the mounting unit 50 comprises the interface plate 66, connected to the fixed insert 65, and the aforementioned receiving surface 40.

Between one retaining and alternate movement means 35 and the next there is a certain angular spacing which is such as to allow the respective mounting unit 50 to be changed with variations in the size of the pickup pad 38 according to the size of the accessory element 7.

As illustrated in FIG. 4d, the forming roller 29 for the pair 13 has, on its outer cylindrical surface, near each of its two longitudinal ends, a ring of suction seats, labelled 51 and 52, which are angularly spaced according to a spacing P and which are located in such a way that each seat 51 is axially aligned with a seat 52, forming therewith a pair of seats labelled 53.

The defined spacing between the seat 51 and the seat 52 is fixed and is equal to the spacing d1 of the lateral flaps 7 of the absorbent article 2. In other words, the defined spacing between the seat 51 and the seat 52 is equal to the spacing of the lateral flaps 7 defined by the second releasing position 42 of the first and second spacer rollers 23 and 24.

The accelerator roller 33 has, on its outer cylindrical surface, a plurality of pairs of suction seats 54 designed to hold down the pairs 13 of lateral flaps 7 formed by the forming roller 29.

Each pair of seats 54 is mounted on a radial shaft 55 which, as the accelerator roller 33 rotates, oscillates about an axis parallel to the second direction D2 under the action of actuating cam means (not illustrated). The accelerator roller 33 is of known type and is described in patent application WO2008155618A2 which, for completeness of description, is incorporated herein by reference.

During the operation of the machine 1 illustrated in FIG. 1, the second spacer roller 24 picks up, at the second pickup station 26, the pieces 28b whose long base is directed towards the left, whilst the first spacer roller 23 picks up, at the first pickup station 25, the pieces 28a whose long base is directed towards the right. That way, the first and second spacer rollers 23 and 24 form a respective succession 36 and 37 of pieces 28 which are equioriented and equispaced by the spacing P.

At the first and second release stations 30 and 31, the pickup pads 38 of the first and second spacer rollers 23 and 24 are located at the second releasing position 42.

During the rotation of the first spacer roller 23 from the first pickup station 25 to the first release station 30, the lateral flaps 7 are translated through the agency of the pickup pads 38 from the first receiving position 41 to the second releasing position 42 along the second axis D2 in a first direction indicated by the arrow F1.

During the rotation of the second spacer roller 24 from the second pickup station 26 to the second release station 31, the lateral flaps 7 are translated through the agency of the pickup pads 38 from the first receiving position 41 to the second releasing position 42 along the second axis D2 in a second direction indicated by the arrow F2, opposite the first direction F1.

That way, the pickup pads 38, driven by the respective linear motors 39, space the lateral flaps 7 from each other until reaching the spacing d1 of the absorbent article 2.

At this point, the suction seat 51 of the forming roller 29 for the pairs 13 picks up the lateral flap 7 at the first release station 30 and the suction seat 52 of the forming roller 29 for the pairs 13 picks up the lateral flap 7 at the second release station 31 in order to form the pairs 13 of lateral flaps 7 to be applied along the continuous web 10.

Since the lateral flaps 7 are already suitably spaced and oriented, the forming roller 29 for the pairs 13 holds down and conveys the paws 13 from the second release station 31 to the first transfer station 34.

At the first transfer station 34, the pairs of seats 54 of the accelerator roller 33 pick up the pairs 13 of lateral flaps 7 from the forming roller 29.

When the pairs 13 are transferred, the tangential speed of the pairs of seats 54 of the accelerator roller 33 is the same as that of the forming roller 29. When the pairs 13 of lateral flaps 7 are applied, on the other hand, the tangential speed of the pairs of seats 54 coincides with the feed speed of the web 10, so that the spacing of the pairs 13 of flaps 7 passes from the value P to the value P1, coinciding with the spacing of the lengths of the web 10 constituting the single absorbent articles 2.

At the feed station 12 the pairs 13 are applied to the continuous web 10.

With reference in particular to FIG. 2, the second embodiment of the machine 1, like the first embodiment illustrated in FIG. 1, comprises the above described feed device 16, conveyor roller 21 separating device 22 and accelerator roller 33.

More specifically, the second embodiment differs from the first embodiment in that it does not have the forming roller 29 for the pairs 13 tangent to the first spacer roller 23 and to the second spacer roller 24.

Alternatively to the first embodiment, the conveying unit 18 comprises a first transfer roller 56 and a second transfer roller 59.

The first transfer roller 56 is substantially tangent to the first spacer roller 23 at a first feed station 57, and substantially tangent to the accelerator roller 33 at a second transfer station 58.

The second transfer roller 59 is substantially tangent to the second spacer roller 24 at a second feed station 60, and substantially tangent to the accelerator roller 33 at a third transfer station 61.

In this case, the accelerator roller 33 constitutes an accelerator conveyor which also forms the pairs 13 of lateral flaps 7.

The first and second transfer rollers 56 and 59, which both rotate clockwise about their respective axes 56a and 59a, have respective fixed suction seats 62 and 63 along their outer cylindrical surfaces.

During the operation of the machine 1 according to the second embodiment, at the first feed station 57, the suction seats 62 of the first transfer roller 56 pick up the lateral flaps 7 from the pickup pads 38 of the first spacing roller 23 located at the second releasing position 42.

The suction seats 62 of the first transfer roller 56 hold down convey the lateral flaps 7 from the first feed station 57 to the second transfer station 58.

At the same time, at the second feed station 60, the suction seats 63 of the second transfer roller 59 pick up the lateral flaps 7 from the pickup pads 38 of the second spacing roller 24 located at the second releasing position 42.

The suction seats 63 of the second transfer roller 59 hold down and convey the lateral flaps 7 from the second feed station 60 to the third transfer station 61.

At this point, the pair of seats 54 of the accelerator roller 33 picks up the lateral flaps 7 from the second transfer roller 59 at the third transfer station 61, and the pair of seats 54 then picks up the lateral flaps 7 from the first transfer roller 56 at the second transfer station 58, thus forming the pair 13 of lateral flaps 7.

When the flaps 7 are transferred, at the second and third transfer stations 58 and 61, the tangential speed of the pairs of seats 54 is the same as that of the first and second transfer rollers 56 and 59. On the other hand, when the pairs 13 of lateral flaps 7 are applied, at the feed station 12, the tangential speed of the pairs of seats 54 coincides with the feed speed of the continuous web 10, so that the spacing of the pairs 13 of flaps 7 passes from the value P to the value P1, coinciding with the spacing of the lengths of the continuous web 10 constituting the single absorbent articles 2.

Advantageously, the configuration of the rollers of the forming and application unit 14 of the second embodiment makes it possible to obtain higher production speeds than that of the first embodiment.

From the foregoing description, it is evident that this invention overcomes the disadvantages described above with reference to the prior art.

The linear motors 39 which drive the pickup pads 38 of the first and second spacer rollers 23 and 24 make it possible to space the lateral flaps 7 from each other with a single translational movement until reaching the mutual spacing d1 suitable for the size of the absorbent article 2, that is to say, both for nappies for children and nappies for adults.

Thus, when changing over to making absorbent articles 2 of a different size, the spacer rollers 23 and 24 of the machine 1 need not be substituted, since the linear motors 39 allow the stroke defined by the first receiving pickup position 41 and by the second release position 42 to be adapted according to the size of the absorbent article 2.

As regards adapting the configuration of the machine 1 to the size of the lateral flaps 7, that is, to the variation of the longitudinal dimension of the flap 7, all that needs to be done is substitute the pickup pads 38 of the first and second spacer rollers 23 and 24 by substituting the mounting unit 50.

Advantageously, the configuration of the rollers of the forming and application unit 14 of the second embodiment makes it possible to adapt the machine 1 upon changeover to an article 2 of a different size, while keeping fixed the distance d of the axes 23a e 24a from each other and varying only the position of the axes 56a and 59a of the first and second transfer rollers 56 and 59.

The machine 1 according to the invention allows changeover to be effected without substituting the first and second spacer rollers 23 and 24 but simply adapting them to the size of the absorbent articles 2 by moving the pickup pads through the agency of the linear motors 39 and thanks to the interchangeability of the mounting unit which allows changeover to be effected quickly, limiting the down as of the machine 1.

The invention claimed is:

1. A machine for making absorbent sanitary articles comprising:
   a feed conveyor on which a continuous web of material for making the absorbent articles is advanced along a feed line in a first direction,
   a cutting element by which the continuous web is divided into single lengths that will make up single absorbent articles,
   a forming and application unit by which at least one pair of accessory elements for each absorbent article are formed and applied to predetermined zones of the continuous web and spaced from each other by a spacing along the feed line;
   the forming and application unit comprising a device for feeding a continuous succession of accessory elements and a conveying unit comprising a plurality of conveyors rotating about respective axes parallel to a second direction transversal to the feed direction of the continuous web;
   the conveying unit comprising a conveyor roller for the continuous succession of accessory elements, a separating device defined by a first spacer roller and a second spacer roller which are substantially tangent to the conveyor roller at a first pickup station and a second pickup station, respectively;
   the first and the second spacer rollers including retaining and alternate movement units by which single accessory elements are alternately held and moved along a direction parallel to the second direction in order to form respective successions of accessory elements;
   at least one forming roller adapted to receive respective accessory elements from the first and second spacer rollers and to make up a succession of pairs of accessory elements aligned with each other along the second direction;

the retaining and alternate movement units including respective pickup pads which are slidable along the second direction;

each pickup pad including a suction surface for receiving the respective accessory element and being movable from a first receiving position to a second releasing position; the second releasing position defining a mutual spacing between the accessory elements;

for each pickup pad, a respective linear electric motor attached to a respective one of the first and the second spacer rollers to rotate with the respective one of the first and the second spacer rollers, the respective linear electric motor including a fixed portion fixed to the respective one of the first and the second spacer rollers and a movable portion movable along an operating axis parallel to the second direction and connected to the pickup pad for driving the pickup pad in a direction parallel to the second direction, wherein the fixed portion rotates together with the respective one of the first and the second spacer rollers, and the movable portion is movable axially along the operating axis and rotationally with the respective one of the first and the second spacer rollers and is rotationally fixed with respect to the fixed portion;

a controller operatively connected to the respective linear motor and programmed to operate the respective linear motor to have an axial stroke defined by the first receiving pickup position and the second release position so that controller variably controls the axial stroke of the respective linear motor according to a size of the absorbent article.

2. The machine according to claim 1, wherein the conveying unit comprises a forming roller for making up the pairs of accessory elements and substantially tangent to the first spacer roller and to the second spacer roller at a first and a second releasing station, respectively.

3. The machine according to claim 2, wherein the conveying unit comprises an accelerator roller which is substantially tangent to the forming roller at a first transfer station.

4. The machine according to claim 1, wherein the conveying unit comprises a first and a second transfer roller for the accessory elements; the first transfer roller being substantially tangent to the first spacer roller at a first feed station and the second transfer roller being substantially tangent to the second spacer roller at a second feed station.

5. The machine according to claim 4, wherein the conveying unit comprises an accelerator roller which is substantially tangent to the first transfer roller at a second transfer station and to the second transfer roller at a third transfer station.

6. The machine according to claim 1, wherein each of the retaining and alternate movement units comprises a mounting unit for the respective pickup pad; the mounting unit being interchangeable with variations in a size of the pickup pad according to a size of the accessory element.

7. The machine according to claim 6, wherein the conveying unit comprises a forming roller for making up the pairs of accessory elements and substantially tangent to the first spacer roller and to the second spacer roller at a first and a second releasing station, respectively.

8. The machine according to claim 7, wherein the conveying unit comprises an accelerator roller which is substantially tangent to the forming roller at a first transfer station.

9. The machine according to claim 6, wherein the conveying unit comprises a first and a second transfer roller for the accessory elements; the first transfer roller being substantially tangent to the first spacer roller at a first feed station and the second transfer roller being substantially tangent to the second spacer roller at a second feed station.

10. The machine according to claim 9, wherein the conveying unit comprises an accelerator roller which is substantially tangent to the first transfer roller at a second transfer station and to the second transfer roller at a third transfer station.

11. The machine according to claim 6, wherein the retaining and alternate movement units are distributed uniformly according to a predetermined spacing along cylindrical surfaces of the first and second spacer rollers, there being between adjacent retaining and alternate movement units a predetermined angular distance to allow the respective mounting unit to be changed with variations in the size of the pickup pad according to the size of the accessory element.

12. The machine according to claim 11, wherein the conveying unit comprises a forming roller for making up the pairs of accessory elements and substantially tangent to the first spacer roller and to the second spacer roller at a first and a second releasing station, respectively.

13. The machine according to claim 12, wherein the conveying unit comprises an accelerator roller which is substantially tangent to the forming roller at a first transfer station.

14. The machine according to claim 11, wherein the conveying unit comprises a first and a second transfer roller for the accessory elements; the first transfer roller being substantially tangent to the first spacer roller at a first feed station and the second transfer roller being substantially tangent to the second spacer roller at a second feed station.

15. The machine according to claim 14, wherein the conveying unit comprises an accelerator roller which is substantially tangent to the first transfer roller at a second transfer station and to the second transfer roller at a third transfer station.

16. The machine according to claim 11, wherein each pickup pad runs in a respective guide and is linked to a conduit connected to a source of suction and to an actuating rod of the respective linear motor; the mounting unit of the pickup pad comprising a central body connected to a respective fixed insert, the fixed insert being connected to the respective conduit and running in the respective guide.

17. The machine according to claim 16, wherein the conveying unit comprises a forming roller for making up the pairs of accessory elements and substantially tangent to the first spacer roller and to the second spacer roller at a first and a second releasing station, respectively.

18. The machine according to claim 17, wherein the conveying unit comprises an accelerator roller which is substantially tangent to the forming roller at a first transfer station.

19. The machine according to claim 16, wherein the conveying unit comprises a first and a second transfer roller for the accessory elements; the first transfer roller being substantially tangent to the first spacer roller at a first feed station and the second transfer roller being substantially tangent to the second spacer roller at a second feed station.

20. The machine according to claim 19, wherein the conveying unit comprises an accelerator roller which is substantially tangent to the first transfer roller at a second transfer station and to the second transfer roller at a third transfer station.

\* \* \* \* \*